(12) United States Patent
Ishikawa et al.

(10) Patent No.: US 7,147,629 B2
(45) Date of Patent: Dec. 12, 2006

(54) DISPOSABLE DIAPER

(75) Inventors: Hiroki Ishikawa, Kagawa-ken (JP); Akiyoshi Kinoshita, Kagawa-ken (JP); Toru Oba, Kagawa-ken (JP); Yasuhiko Kenmochi, Kagawa-ken (JP)

(73) Assignee: Uni-Charm Corporation, Ehime-ken (JP)

( * ) Notice: Subject to any disclaimer, the term of this patent is extended or adjusted under 35 U.S.C. 154(b) by 534 days.

(21) Appl. No.: 10/289,600

(22) Filed: Nov. 7, 2002

(65) Prior Publication Data

US 2003/0130639 A1  Jul. 10, 2003

(30) Foreign Application Priority Data

Nov. 9, 2001  (JP) .............................. 2001-345265

(51) Int. Cl.
*A61F 13/15* (2006.01)
(52) U.S. Cl. .............................. 604/385.101; 604/367; 604/368; 604/375; 604/378
(58) Field of Classification Search ................ 604/367, 604/385.101, 368, 366, 375, 378, 369; 428/212, 428/218, 171, 172, 220, 402, 403
See application file for complete search history.

(56) References Cited

U.S. PATENT DOCUMENTS

| | | | |
|---|---|---|---|
| 4,610,678 A | 9/1986 | Weisman et al. | |
| 5,439,458 A | 8/1995 | Noel et al. | |
| 5,855,571 A | * 1/1999 | Steger et al. | 604/368 |
| 6,017,336 A | * 1/2000 | Sauer | 604/385.01 |

FOREIGN PATENT DOCUMENTS

| | | |
|---|---|---|
| EP | 1 110 528 A2 | 12/2000 |
| EP | 1 312 325 A2 | 11/2002 |
| JP | 52-20692 | 2/1977 |
| WO | WO 99/22685 | 5/1999 |

* cited by examiner

*Primary Examiner*—Jacqueline F. Stephens
(74) *Attorney, Agent, or Firm*—Butzel Long

(57) ABSTRACT

A disposable diaper has an absorbent core. The core contains therein hydrophilic fibers of 30–70 wt % and super-absorbent polymer particles of 70–30 wt %. Of the super-absorbent particles, first super-absorbent polymer particles having a relatively long liquid-absorbing duration lying in a middle zone of the core as viewed in a transverse direction as well as in a thickness direction of the core to form a polymer phase and second super-absorbent polymer particles having a relatively short liquid-absorbing duration lying in the core above, below and laterally outside the polymer phase to form a mixture phase containing therein the hydrophilic fibers mixed therewith.

6 Claims, 3 Drawing Sheets

DISPOSABLE DIAPER

BACKGROUND OF THE INVENTION

This invention relates to disposable diapers for absorption and containment of excrement.

Japanese Patent Publication No. 1977-20692A disclosed several embodiments of a body fluid absorbent core used in a sanitary napkin, each comprising fluff pulp fibers and super-absorbent polymer particles. These embodiments include the core comprising the super-absorbent polymer particles and the fluff pulp fibers homogeneously mixed together and the core comprising a layer of aggregated super-absorbent polymer particles and two layers of fluff pulp fibers sandwiching the layer of polymer particles from above and below, respectively.

It is well known that a water holding capacity of the super-absorbent polymer particles is substantially higher than a water holding capacity of fluff pulp fibers and use of the super-absorbent polymer particles is effective to prevent a so-called rewet phenomenon. However, once having formed a gel block, the super-absorbent polymer particles may have an effect opposite to what was expected for these polymer particles. To avoid this, it is preferred for the core comprising a mixture of the super-absorbent polymer particles and the fluff pulp fibers to mix them together as homogeneously as possible and thereby to prevent the individual super-absorbent polymer particles from coming in contact one with another. To this end, however, a problem is faced that a content of the super-absorbent polymer particles in the core should be inevitably limited. As one of measures to solve this problem, it is well known to use a mixture of the super-absorbent polymer particles having a relatively high absorption rate and the super-absorbent polymer particles having a relatively low absorption rate. In this case, two different types of super-absorbent polymer particles must be mixed with the fluff pulp fibers as homogeneously as possible. Here arises another problem that a significant difference in specific gravity between the super-absorbent polymer particles and the fluff pulp fibers makes it difficult to mix them to a desired homogeneity. The sandwich type core including the layer of aggregated super-absorbent polymer particles, on the other hand, is accompanied with a problem that the super-absorbent polymer particles readily form the gel block as these polymer particles absorb body fluids and a certain amount of body fluids stagnates above the gel block. The amount of body fluids stagnating above the gel block may flow back toward a sanitary napkin or a diaper wearer's skin and the super-absorbent polymer particles may function in the reverse way when a body weight of the wearer is exerted upon such core. In consequence, a remarkable rewet phenomenon may occur and give the wearer uncomfortable feeling of wetness.

SUMMARY OF THE INVENTION

In view of the problems as have been described above, it is an object of this invention to provide the disposable diaper in which the body fluid absorbent core containing therein the super-absorbent polymer particles has an improved preventive effect against leak of body fluids and so-called the rewet phenomenon.

According to this invention, there is provided a disposable diaper having a front waist region, a rear waist region and a crotch region extending between the two waist regions, each of the regions being formed with a body facing surface and a garment facing surface, and a liquid-pervious sheet defining the body facing surface in the crotch region is provided on an inner surface of the liquid-pervious sheet with an absorbent core.

The core comprises hydrophilic fibers of 30–70 wt % and super-absorbent polymer particles of 70–30 wt %, the super-absorbent polymer particles comprising first polymer particles having a relatively long liquid-absorbing duration and second polymer particles having a relatively short liquid-absorbing duration, wherein a polymer phase primarily comprising the first polymer particles lies in a middle zone of the core as viewed in a transverse direction as well as in a thickness direction of the core and a mixture phase comprising the hydrophilic fibers and the second polymer particles 2 mixed therewith lies above, below and laterally outside the polymer phase.

This invention includes the following embodiments.

The first and second polymer particles having a liquid-permeating duration of 15–100 seconds, the first polymer particles have a liquid-absorbing duration of 30–60 seconds and the second polymer particles has a liquid-absorbing duration of 3–30 seconds so that a difference in the liquid-absorbing duration between the first and second polymer particles is at least 5 seconds.

Assumed that a sum of weights of the first polymer particles and the second polymer particles in the core is 100, a ratio of the first and second polymer particles is (20–70) (80–30).

The polymer phase has, in the crotch region, a width corresponding to 40–90% of a full width of the core.

The core has a longitudinal direction orthogonal to the transverse direction and the polymer phase has a length corresponding to 40–100% of a dimension of the core as measured in the longitudinal direction.

The core has a thickness of 3–15 mm and the polymer phase has a thickness of 0.3–3.5 mm.

The parameter "liquid-absorbing duration" of the super-absorbent polymer particles herein described is measured using a method as follows. First, 50 g of physiologic saline poured into a 100 ml beaker is stirred at a temperature of 25° C. by a magnetic stirrer with a rotor sized in 8 mm diameter ×30 mm length and having a revolution speed of 600 rpm. Then 2.0 g of the super-absorbent polymer particles is put into the beaker and an elapsed time is measured before revolving vortex of the physiologic saline disappears and the saline level becomes flat. The time elapse measured in this manner is obtained as "liquid-absorbing duration".

The parameter "liquid-permeating duration" of the super-absorbent polymer particles herein described is measured using a method as follows. First, a nylon filter of 250 meshes is attached to a bottom side of a cylinder having a diameter of 39 mm and 1 g of the super-absorbent polymer particles is evenly spread. Then, 10 seconds are spent to pour 50 g of the physiologic saline into the cylinder. It is assumed that the super-absorbent polymer particles are saturated after such a step of pouring has been repeated six times at time intervals of 3 minutes. 3 minutes after the sixth step of pouring, 10 seconds are spent to pour 50 g of the physiologic saline into the cylinder and a time period elapsing until substantially total amount of this physiologic saline permeates the filter is measured. The time elapse measured in this manner is obtained as "liquid-permeating duration".

DETAILED DESCRIPTION OF THE PREFERRED EMBODIMENTS

Details of a disposable diaper according to this invention will be more fully understood from the description given hereunder with reference to the accompanying drawings.

Figure 1:
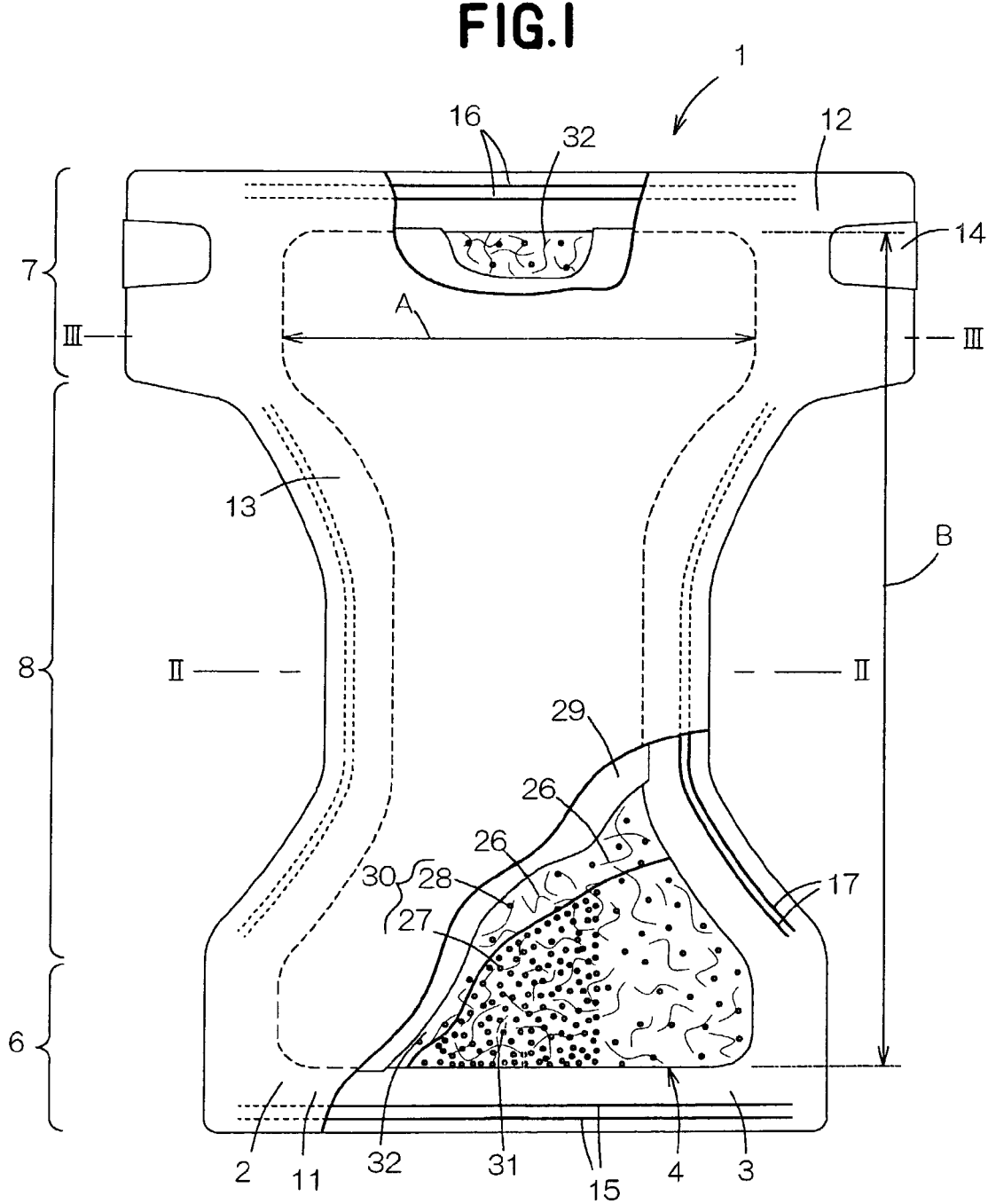
FIG. 1 is a plan view of a partially cutaway disposable diaper according to this invention.

FIG. 1 is a plan view of a partially cutaway disposable diaper 1 according to the principle of this invention. This diaper 1 is of open-type and comprises a liquid-pervious topsheet 2 defining a body facing surface, a liquid-impervious backsheet 3 defining a garment facing surface and an absorbent core 4 interposed between the two sheets 2, 3. Portions of the top- and backsheets 2, 3 extending outward beyond a peripheral edge of the core 4 are placed upon and bonded to each other to form front and rear end flaps 11, 12 and a pair of side flaps 13. The diaper 1 is composed, in its longitudinal direction (i.e., vertical direction as viewed in FIG. 1), a front waist region 6, a rear waist region 7 and a crotch region 8 extending between the two waist-regions 6, 7. In the rear waist region 7, the pair of side flaps 13 are provided with tape fasteners 14 attached thereto, respectively. In the front and rear end flaps 11, 12 and the side flaps 13 in the crotch region 8, the waist-surrounding elastic members 15, 16 and the leg-surrounding elastic members 17 are secured in a stretched state to the inner surface of at least one of the top- and backsheets 2, 3.

Figure 2:
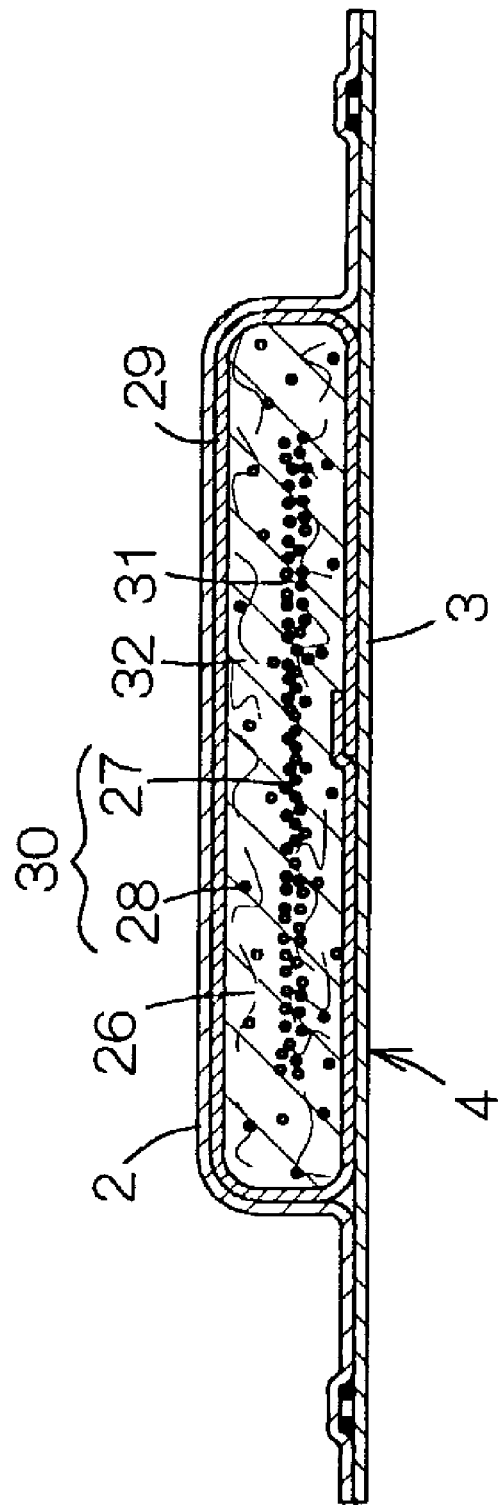
FIG. 2 is a cross-sectional view taken along a line II—II in FIG. 1.
Figure 3:
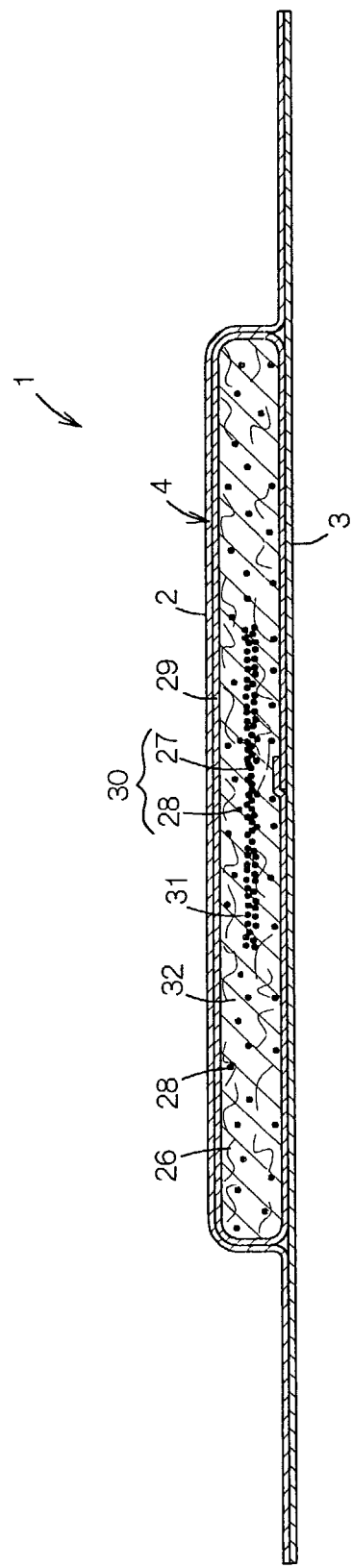
FIG. 3 is a cross-sectional view taken along a line III—III in FIG. 1.

FIG. 2 is a cross-sectional view taken along a line II—II in FIG. 1 and FIG. 3 is a cross-sectional view taken along a line III—III in FIG. 1. In the diaper 1, a stock material for the topsheet 2 may be a nonwoven fabric or a porous film. The nonwoven fabric used for this diaper 1 may be selected from a group consisting of thermoplastic synthetic fibers such as polyolefine-, polyester- or polyamide-based thermoplastic synthetic fibers, and polyethylene/polypropylene or polyethylene/polyester conjugated fibers of sheath-and-core type or side-by-side type. It is also possible to use nonwoven fabric of hydrophilically modified these fibers or nonwoven fabric of water-absorbent fibers such as rayon, acetate and cotton. The porous film may be, for example, a polyethylene film.

A stock material for the backsheet 3 may be selected from a group including polyethylene-, polypropylene-, polyester- and polyurethane films, which is preferably of breathable type.

By reference to FIGS. 2 and 3 in conjunction with FIG. 1, it will be apparent that the core 4 has a dimension A in the transverse direction and a dimension B in the longitudinal direction orthogonal to the transverse direction A. The dimension A is relatively large in the front and rear waist regions 6, 7 and relatively small in the crotch region 8 so as to present a so-called hourglass-shape. The core 4 has a thickness preferably in a range of 3–15 mm and its surface opposite to the topsheet 2 has an area in a range of 350–2000 $cm^2$. The core 4 comprises, in addition to hydrophilic fibers 26 such as fluff pulp fibers, super-absorbent polymer particles 30 consisting of first polymer particles 27 and second polymer particles 28. The core 4 is covered with a tissue paper 29 or a high wet strength nonwoven fabric made of hydrophilically modified thermoplastic synthetic fibers.

The hydrophilic fibers 26 occupy 30–70 wt % in the core 4 and may be selected from a group consisting of natural fibers such as fluff pulp fibers, cotton or jute, regenerated fibers such as rayon or acetate, and hydrophilically modified thermoplastic synthetic fibers. The super-absorbent polymer particles 30 occupy 70–30 wt % in the core 4. Of the super-absorbent polymer particles 30, the first polymer particles 27 have a liquid-permeating duration of 15–100 seconds and a liquid-absorbing duration of 30–60 seconds and the second polymer particles 28 have a liquid-permeating duration of 15–100 seconds and a liquid-absorbing duration of 3–30 seconds. A difference in the liquid-absorbing durations between these first and second polymer particles 27, 28 is preferably at least 5 seconds. Assumed that a sum of weights of the first polymer particles and the second polymer particles in the core is 100, a ratio of these first and second polymer particles is in a range of (20–70): (80–30). Phase 31 comprising the hydrophilic fibers of 20–90 wt %, preferably of 30–70 wt % and the polymer particles 27 of 80–10 wt %, preferably of 70–30 wt % is compressed to ensure its density preferably in a range of 0.06–0.15 $g/cm^3$. The hydrophilic fibers 26 may be selected from a group consisting of natural fibers such as fluff pulp fibers, cotton or jute, regenerated fibers such as rayon or acetate and hydrophilically modified thermoplastic synthetic fibers. The polymer particles 27 have a liquid-absorbing duration of 3–30 seconds and a liquid-permeating duration of 15–100 seconds. At least 50 wt % of the first polymer particles 27 and the second polymer particles 28, respectively, have a particle diameter preferably of 250–600 μm.

The first polymer particles 27 define a polymer phase 31 lying in a middle zone of the crotch region 28 as viewed in a thickness direction as well as a transverse direction of the core 4 and the second polymer particles 28 define a mixture phase 32 comprising a substantially homogeneous mixture of the second polymer particles 28 and the hydrophilic fibers 26 and enclosing the polymer phase 31 as viewed in a transverse section of the core 4. In the polymer phase 31, the first polymer particles 27 are used so as to have a basis weight of 50–600 $g/m^2$ and to occupy 90 wt % or more of the polymer phase 31. In other words, the polymer phase 31 primarily comprises the first polymer particles 27. Such polymer phase 31 may contain the hydrophilic fibers 26 and/or the second polymer particles 28 of 10 wt % or less. The polymer phase 31 preferably has, in the crotch region 8, a width corresponding to 40–90% of the core's transverse dimension A and, in the front and rear waist regions 6, 7, a width corresponding to less than 40% of the core's transverse dimension A (See FIG. 3). The polymer phase 31 preferably has a length corresponding to 40–100% of the core's longitudinal dimension B. The polymer phase 31 is compressed preferably so that this phase 31 has a thickness of 0.3–3.5 mm and a density of 0.09–0.47 $g/cm^3$. The mixture phase 32 comprises the hydrophilic fibers 26 of 35–95 wt % and the second polymer particles 28 of 5–65 wt %. The mixture phase 32 is compressed preferably so that this phase 32 has a density of 0.06–0.15 $g/cm^3$.

Now it is assumed that urination occurs on the diaper 1 having such core 4 in which the first polymer particles 27 having the relatively long liquid-absorbing duration are aggregated in the middle zone of the core 4 as viewed in the thickness direction as well as in the transverse direction thereof and the second polymer particles 28 having the relatively short liquid-absorbing duration and mixed with the hydrophilic fibers 26 are distributed outside the first polymer particles 27 as viewed in the thickness direction as well as in the transverse direction of the core 4. Urine discharged on the diaper 1 is absorbed and diffused by the tissue paper 29 lying on the upper surface of the core 4 and, practically at the same time, urine moves toward the mixture phase 32. In the mixture phase 32, urine is rapidly absorbed by the hydrophilic fibers 26 and the second polymer particles 28 having the relatively short liquid-absorbing duration. In the case of using fluff pulp fibers as the hydrophilic fibers 26, the amount of urine having been absorbed by the fibers 26 moves down in the thickness direction of the core 4 more rapidly than the case in which any other material is used as the hydrophilic fibers 26. In the transversely middle zone of the core 4, an amount of urine moving downward permeates the polymer phase 31 to be absorbed by the first polymer particles 27 and a portion of urine passes through the polymer phase 31 to be absorbed by the mixture phase 32 in its zone underlying the polymer phase 31. In the transversely opposite sides of the core 4, a continuity of the mixture phase 32 in the thickness direction of the core 4 allows an amount of urine to move to the bottom of the core 4 and a portion of this amount of urine moves in the transverse direction so as to be absorbed by the mixture phase 32 in its zone underlying the polymer phase 31. Both the first polymer particles 27 and the second polymer particles 28 have a liquid-permeating duration of 15–100 seconds and allow urine to pass through gel blocks, even if these polymer particles 27, 28 form such gel blocks. Therefore, urine can smoothly permeate the mixture phase 32 downward and easily pass through the polymer phase 31.

Urine discharged on the diaper is absorbed by the core 4 in this manner and, more specifically, rapidly absorbed by the hydrophilic fibers 26 and the second polymer particles 28 having the relatively short liquid-absorbing duration in the upper zone of the core 4 in its thickness direction. Such feature is advantageously effective to minimize a possible leakage of urine into the side flaps 13 of the diaper 1 immediately after urination and thereby to realize the diaper 1 substantially free from urine leakage. Generally, the super-absorbent polymer particles having a relatively short liquid-absorbing duration result in the correspondingly low gel strength and the wearer's body weight exerted on the gel block formed by these particles tends to expel the amount of urine having been absorbed thereby out from the core 4. In the core 4 of this diaper 1, on the contrary, the polymer phase 31 is formed by the first polymer particles 27 having a sufficiently long liquid-absorbing duration to retain the amount of urine having been absorbed thereby. In consequence, there is no anxiety that the amount of urine having been absorbed by this polymer phase 31 and the portion of the mixture phase 32 underlying the polymer phase 31 might flow back to the upper surface of the topsheet 2 even when the wearer's body weight is exerted on the core 4. In this way, the diaper 1 adopting such core 4 is improved also with the preventive effect against a so-called rewet phenomenon.

EXAMPLES

In the disposable diaper shown by FIG. 1, the core having its transverse dimension A which is 200 mm in the front and rear waist regions and 100 mm in the crotch region and having its longitudinal dimension B of 600 mm was used to measure the amount of rewet and the minimum amount of urine before urine leakage begins. TABLE 1 shows result of the measurement and composition of the hydrophilic fibers and the super-absorbent polymer particles used for this core. Fluff pulp was used as the hydrophilic fibers, particles a or particles b were used as the first poly particles and particles c were used as the second polymer particles. TABLE 2 shows properties of these particles a, b, c.

The minimum amount of urine before urine leakage begins was measured by the method as follows. First, each EXAMPLE of the disposable diaper was put on a lay figure taking half-faced posture. Then, physiologic saline in substitution for urine was continuously discharged at a flow rate of 10 ml/sec from urination port provided on the lay figure and urine leakage from the diaper was observed to measure an amount of urine before urine leak actually occurs. The measured amount was obtained as the minimum amount of urine.

The amount of so-called rewet was measured by the method as follows. First, the diaper was flattened and a cylinder having an inner diameter of 60 mm and a weight of 750 g was placed on a central zone of the core. Then, 150 ml of physiologic saline was poured into the cylinder from 10 mm above the diaper at a flow rate of 10 ml/sec. After physiologic saline had been absorbed by the core, the cylinder was removed from the core and 5 minutes after start of pouring, checkweighed 100×100 mm paper filter was placed on the same zone of the core as the zone on which the cylinder had been placed. A weight of 3.5 kg/100×100 mm was placed on the paper filter and left as it is for 3 minutes. Thereafter the paper filter was checkweighed to measure an amount of saline having been absorbed by the paper filter for 3 minutes as the amount of rewet (of first step). 10 minutes after start of pouring physiologic saline, the cylinder was placed again on the central zone of the core, 150 ml of physiologic saline 10 seconds was poured into the cylinder and measurement of the amount of saline having been absorbed was repeated to obtain the amount or rewet (of second step). Such operation was repeated once more to obtain the amount of rewet (of third step).

(Controls)

In the place of the core used in EXAMPLES, the core comprising particles a alone, the core comprising particles b alone and the core comprising particles c alone were used. For the diapers using such cores, the amount of rewet and the minimum amount of urine before urine leakage begins were measured by the same method used in EXAMPLES. Result of the measurement is shown in TABLE 1. Distribution of these particles a, b, c in the core was same as in the core of EXAMPLES.

As will be apparent from TABLE 1, the diaper using combination of the first and second polymer particles a, c as the super-absorbent polymer particles exhibits the minimum amount of urine before urine leakage begins larger than the minimum amount of urine exhibited by the diaper provided with the core using the first polymer particles a alone. This means that the former is less liable to urine leakage than the latter (See EXAMPLE 1 and CONTROL 1). It will be also found from TABLE 1 that the diaper provided with the core using combination of the first and second polymer particles a, c exhibits the amount of rewet smaller than the amount of rewet exhibited by the diaper provided with the core using the second polymer particles c alone (See EXAMPLE 1 and CONTROL 3). Furthermore, it will be found from TABLE 1 that the diaper provided with the core using combination of the first and second polymer particles b, c is less liable to urine leakage than the diaper provided with the core using the first polymer particles b (See EXAMPLE 2 and CONTROL 2).

TABLE 1

| | | EXAMPLES | | CONTROLS | | |
|---|---|---|---|---|---|---|
| | | 1 | 2 | 1 | 2 | 3 |
| Super-absorbent polymer particles (g) | | | | | | |
| First polymer particles | a | 11 | — | 24 | — | — |
| | b | — | 9 | — | 19 | — |
| Second polymer particles | c | 13 | 10 | — | — | 24 |
| Hydrophilic fibers (g) Fluff pulp fibers | | 40 | 28 | 40 | 28 | 40 |
| Amount of rewet (g) | | | | | | |
| First step | | 0.2 | 0.5 | 0.2 | 0.5 | 1.1 |
| Second step | | 38 | 42 | 31 | 33 | 49 |
| Third step | | 59 | 62 | 58 | 60 | 69 |
| Minimum amount of urine before leakage occurs | | 350 | 300 | 250 | 200 | 350 |

TABLE 2

| | First polymer particles | | Second polymer particles |
|---|---|---|---|
| | Particles a | Particles b | Particles c |
| Liquid-absorbing duration (sec) | 53 | 36 | 14 |
| Liquid-permeating duration (sec) | 25 | 48 | 71 |

The disposable diaper according to this invention is primarily characterized in that the core generally comprises hydrophilic fibers and super-absorbent polymer particles wherein the super-absorbent polymer particles consist of the first polymer particles of which the liquid-permeating duration is relatively short and the liquid-absorbing duration is relatively long and the second polymer phase of which both the liquid-permeating duration and the liquid-absorbing duration are relatively short. With such a unique arrangement, the core is effective to prevent urine leakage as well as a so-called rewet phenomenon from occurring in the diaper.

What is claimed is:

1. A disposable diaper having a body facing surface and a garment facing surface, said disposable diaper comprising: a front waist region; a rear waist region; a crotch region extending between said front and rear waist regions; and an absorbent core provided between said body facing surface and said garment facing surface; said absorbent core comprising hydrophilic fibers of 30–70 wt % and super-absorbent polymer particles of 70–30 wt %, said super-absorbent polymer particles comprising first polymer particles having a relatively long liquid-absorbing duration and second polymer particles having a relatively short liquid-absorbing duration, wherein substantially all said first polymer particles are contained within a single first zone in a middle zone of said core as viewed in a transverse direction as well as in a thickness direction of said core and a mixture of said hydrophilic fibers and said second polymer particles defines a second surround zone that lies above, below and laterally outside said first zone.

2. The disposable diaper according to claim 1, wherein said first and second polymer particles having a liquid-permeating duration of 15–100 seconds, said first polymer particles have a liquid-absorbing duration of 30–60 seconds and said second polymer particles has a liquid-absorbing duration of 3–30 seconds so that a difference in the liquid-absorbing duration between these first and second polymer particles is at least 5 seconds.

3. The disposable diaper according to claim 1, wherein, assumed that a sum of weights of said first polymer particles and said second polymer particles in said core is 100, a ratio of these first and second polymer particles is in a range of (20–70):(80–30).

4. The disposable diaper according to claim 1, wherein said first zone has, in said crotch region, a width corresponding to 40–90% of a full width of said care.

5. The disposable diaper according to claim 1, wherein said core has a longitudinal direction orthogonal to said transverse direction and said first zone has a length corresponding to 40–100% of a dimension of said core as measured in said longitudinal direction.

6. The disposable diaper according to claim 1, wherein said core has a thickness of 3–15 mm and said first zone has a thickness of 0.3–3.5 mm.

* * * * *